United States Patent
Yang et al.

(10) Patent No.: US 9,775,515 B2
(45) Date of Patent: Oct. 3, 2017

(54) SYSTEM AND METHOD FOR MULTI-SCALE CLOSED-LOOP EYE TRACKING WITH REAL-TIME IMAGE MONTAGING

(71) Applicants: Qiang Yang, Rochester, NY (US); Jie Zhang, Pittsford, NY (US)

(72) Inventors: Qiang Yang, Rochester, NY (US); Jie Zhang, Pittsford, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 15/158,803

(22) Filed: May 19, 2016

(65) Prior Publication Data

US 2016/0345828 A1 Dec. 1, 2016

Related U.S. Application Data

(60) Provisional application No. 62/167,506, filed on May 28, 2015.

(51) Int. Cl.

| | |
|---|---|
| *A61B 3/14* | (2006.01) |
| *A61B 3/10* | (2006.01) |
| *A61B 3/00* | (2006.01) |
| *A61B 3/15* | (2006.01) |
| *A61B 3/113* | (2006.01) |

(Continued)

(52) U.S. Cl.
CPC ............ *A61B 3/152* (2013.01); *A61B 3/0025* (2013.01); *A61B 3/113* (2013.01); *A61B 3/1225* (2013.01); *G02B 26/105* (2013.01)

(58) Field of Classification Search
USPC .................................................. 351/200–246
See application file for complete search history.

(56) References Cited

U.S. PATENT DOCUMENTS

| | | | |
|---|---|---|---|
| 2003/0053026 A1* | 3/2003 | Roorda ..................... | G01J 9/00 351/206 |
| 2011/0234978 A1* | 9/2011 | Hammer ................ | A61B 3/102 351/208 |

(Continued)

OTHER PUBLICATIONS

Sochor, Matthew, "Automatic 2d Rigid Body Image Registration," 2008 www.mathworks.com/matlabcentral/fileexchange/19086-automatic-2d-rigid-body-image-registration?requestedDomain=www.mathworks.com.

(Continued)

*Primary Examiner* — Mohammed Hasan
(74) *Attorney, Agent, or Firm* — Harris Beach PLLC

(57) ABSTRACT

A system for multi-scale closed-loop eye tracking to compensate for translation and rotation motion while imaging in vivo a surface area of an internal structure of an eye of a subject includes a narrow field imaging device optically coupled to an optical path to receive light reflected from the surface area of the structure of the eye. A wide field camera is optically coupled to the optical path by a beam splitter disposed in the optical path. A tracking mirror is disposed in the optical path between the beam splitter and the structure of the eye. A control process algorithm actively compensates substantially in real time for both translational and rotational movements of the eye. A system where a torsional correction device causes a rotating movement of a subject's head and a method for multi-scale closed-loop eye tracking are also described.

21 Claims, 9 Drawing Sheets

(51) Int. Cl.
*A61B 3/12* (2006.01)
*G02B 26/10* (2006.01)

(56) References Cited

U.S. PATENT DOCUMENTS

| | | | | |
|---|---|---|---|---|
| 2013/0301002 A1* | 11/2013 | Gruppetta | ................ | A61B 3/12 351/206 |
| 2013/0308098 A1* | 11/2013 | Levecq | ................ | A61B 3/1015 351/206 |
| 2015/0070655 A1* | 3/2015 | Rossi | ....................... | A61B 3/12 351/214 |

OTHER PUBLICATIONS

Wilson, Cyrus A. et al., A Correlation-Based Approach to Calculate Rotation and Translation of Moving Cells, 2006 IEEE Transactions on Image Processing, vol. 15, No. 7 pp. 1939-1951.

* cited by examiner

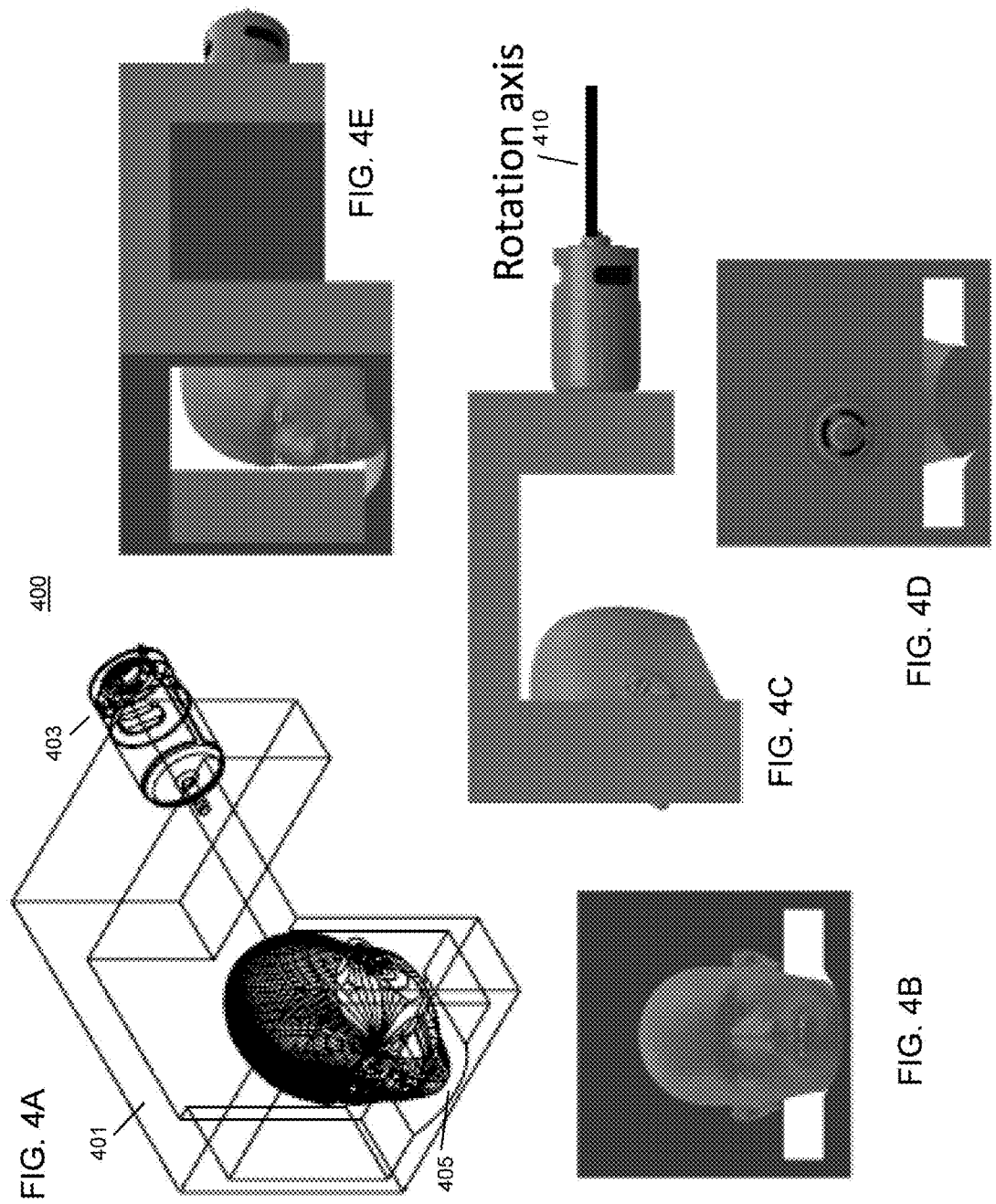

SYSTEM AND METHOD FOR MULTI-SCALE CLOSED-LOOP EYE TRACKING WITH REAL-TIME IMAGE MONTAGING

CROSS-REFERENCE TO RELATED APPLICATIONS

This application claims priority to and the benefit of co-pending U.S. provisional patent application Ser. No. 62/167,506, SYSTEM AND METHOD FOR MULTI-SCALE CLOSED-LOOP EYE TRACKING WITH REAL-TIME IMAGE MONTAGING, filed May 28, 2015, which application is incorporated herein by reference in its entirety.

STATEMENT REGARDING FEDERALLY FUNDED RESEARCH OR DEVELOPMENT

This invention was made with government support under EY021166 and EY001319 awarded by the National Institutes of Health. The government has certain rights in the invention.

FIELD OF THE APPLICATION

The application relates to compensation of eye motion during ophthalmic imaging and particularly to a multi-scale closed-loop eye tracking system and method to compensate for eye motion while obtaining multiple images of a structure of the human eye.

BACKGROUND

When imaging the human eye in vivo, the patient is typically asked to fixate on a fixation target of a viewing surface. For relatively narrow field of view imaging, the patient is asked to fixate on a number of successive targets in rows and columns on the fixation graphic. The process of fixating on one or more fixation targets can be mentally and physically exhausting. Despite the patient's best efforts, the patient's eyes move in both translation and rotation during the imaging process.

Patients with eye disease are more likely to need imaging of damaged structures of their eyes. Unfortunately, it can be more difficult such patients with disease damaged eyes to fixate on a target. Also, because of severe damage to parts of the eye, it may not be possible to fixate on some of the fixation targets.

SUMMARY

According to one aspect, a system for multi-scale closed-loop eye tracking to compensate for translation and rotation motion while imaging in vivo a surface area of an internal structure of an eye of a subject includes a narrow field imaging device optically coupled to an optical path to receive light reflected from the surface area of the structure of the eye. A wide field camera is optically coupled to the optical path by a beam splitter disposed in the optical path. A tracking mirror is disposed in the optical path between the beam splitter and the structure of the eye. A torsional correction device is mechanically coupled to one or more optical components of the system. A control process algorithm runs on a computer. The computer is communicatively coupled to the wide field camera and the narrow field imaging device and the tracking mirror and the torsional correction device. The control process algorithm causes movements of the tracking mirror and the torsional correction device to actively compensate substantially in real time for both translational and rotational movements of the eye at least in part based on feedback images from the wide field camera and the narrow field imaging device.

In one embodiment, the system for multi-scale closed-loop eye tracking further includes an additional steering mirror disposed in the optical path between the narrow field imaging device and the beam splitter, the additional steering mirror communicatively coupled to the computer and controlled by the control process algorithm to provide an additional translational correction.

In another embodiment, the wide field camera includes a Fundus camera.

In yet another embodiment, the narrow field imaging device includes an AOSLO imaging apparatus.

In yet another embodiment, the AOSLO imaging apparatus is optically turned off when an AOSLO scanner runs out of an imaging FOV.

In yet another embodiment, the system for multi-scale closed-loop eye tracking further includes an over-sampling analog to digital converter (A/D) in combination with a pixel-binning process algorithm which runs on a pixel-binning hardware to increase a signal to noise ratio (SNR) of a raw image from the AOSLO imaging apparatus.

In yet another embodiment, the tracking mirror includes at least one or more galvano scanning mirrors.

In yet another embodiment, the wide field camera and the narrow field imaging device are mounted on a rotational stage mechanically coupled to the torsional correction device.

In yet another embodiment, either of the wide field camera or the narrow field imaging device, is mounted on a rotational stage mechanically coupled to the torsional correction device.

In yet another embodiment, the torsional correction device includes a motor.

In yet another embodiment, the system includes an integration of multiple channels of data I/O on a single personal computer (PC).

According to another aspect, a system for multi-scale closed-loop eye tracking to compensate for translation and rotation motion while imaging in vivo a surface area of an internal structure of an eye of a subject where a subject's head is supported by the system includes a narrow field imaging device optically coupled to an optical path to receive light reflected from the surface area of the structure of the eye. A wide field camera is optically coupled to the optical path by a beam splitter disposed in the optical path. A tracking mirror is disposed in the optical path between the beam splitter and the structure of the eye. A torsional correction device is mechanically coupled to a mechanical fixture to support and to rotatingly move the subject's head. A control process algorithm runs on a computer. The computer is communicatively coupled to the wide field camera and the narrow field imaging device and the tracking mirror and the torsional correction device. The control process algorithm causes movements of the tracking mirror and the torsional correction device to actively compensate substantially in real time for both translational and rotational movements of the eye at least in part based on feedback images from the wide field camera and the narrow field imaging device.

In one embodiment, the mechanical fixture includes a chin rest and the torsional correction device causes a rotation of the chin rest.

In another embodiment, the torsional correction device includes a motor.

According to yet another aspect, a method for multi-scale closed-loop eye tracking to compensate for translation and rotation motion while imaging in vivo a surface area of an internal structure of an eye of a subject's head includes: providing a narrow field imaging device optically coupled to an optical path to receive light reflected from the surface area of the structure of the eye, a wide field camera optically coupled to the optical path by a beam splitter disposed in the optical path, a tracking mirror disposed in the optical path between the beam splitter and the structure of the eye, a torsional correction device, and a control process algorithm running on a computer; calculating by computer a translation and a rotation of the eye at least in part from an image received from the wide field camera and the narrow field imaging device; and setting by computer a position of the tracking mirror to compensate for the translation of the eye and setting by computer a rotational movement of the torsional correction device, to compensate for the rotation of the eye.

In one embodiment, the step of setting includes setting by computer the torsional correction device which rotates both of the wide field camera and the narrow field imaging device to compensate for the rotation of the eye.

In another embodiment, the step of setting includes setting by computer the torsional correction device which rotates the wide field camera or the narrow field imaging device to compensate for the rotation of the eye.

In yet another embodiment, the step of setting includes setting by computer the torsional correction device which rotates a mechanical fixture to rotate the subject's head to compensate for the rotation of the eye.

In yet another embodiment, the step of setting includes setting by computer the torsional correction device which rotates a chin mount of the mechanical fixture to rotate the subject's head to compensate for the rotation of the eye.

The foregoing and other aspects, features, and advantages of the application will become more apparent from the following description and from the claims.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

FIG. 4A shows an isometric drawing of an exemplary rotating chin rest system;

FIG. 4B is a drawing showing a front face view of a human subject resting his chin in chin rest;

FIG. 4C shows a side view of the rotating mount and motor of FIG. 4B;

FIG. 4D shows a rear view of the rotating mount and motor of FIG. 4B;

FIG. 4E shows an angled side view of the rotating mount and motor of FIG. 4B;

DETAILED DESCRIPTION

Definitions

Figure 1:
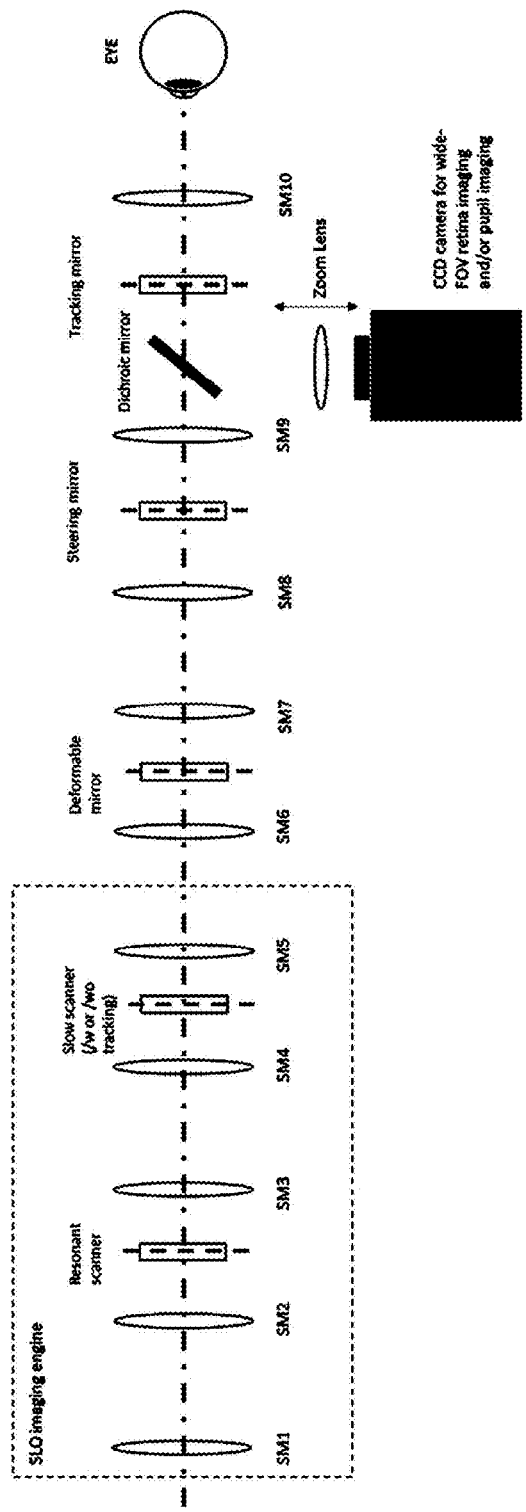
FIG. 1 shows an optical layout of an exemplary closed-loop control system using both and adaptive optics scanning laser ophthalmoscope (AOSLO) and a wide field of view (wide-FOV) camera.

Fundus camera: A fundus camera is an imaging device which can be used to create a photograph of the interior surface of the eye, including the retina, optic disc, macula, and posterior pole (i.e. the fundus). A fundus camera usually images a wide field of view (wide-FOV) of a surface of the eye, in tens of degrees. A fundus camera can be implemented as a snapshot system where the image sensor takes one whole image at a time, or a wide-FOV camera can be implemented in a scanning system. A scanning black/white fundus camera has been implemented in one embodiment of our experimental systems. A color snapshot fundus camera will be implemented according to the new system and method for multi-scale closed-loop eye tracking with real-time image montaging as described hereinbelow. A fundus camera is but one example of a suitable type of wide-FOV camera. Any other type of suitable wide-FOV camera can be used.

AOSLO: An adaptive optics scanning laser ophthalmoscope (AOSLO) is an instrument that uses adaptive optics to remove optical aberrations of the eyes and to obtain high-resolution images from the retina. The imaging field of view (FOV) of AOSLO usually ranges from about 0.5° to 3°, although the scanning field of view can be slightly larger. An AOSLO is an example of a small-FOV camera. Any other type of suitable small-FOV camera can be used.

AOSLO image registration, averaging and integration: A single frame of image from AOSLO usually includes relatively large distortion and relatively high noise. To achieve a high signal-to-noise ratio (SNR) retinal image using an AOSLO apparatus for further qualitative and/or quantitative analysis, multiple single images are typically acquired and then averaged together or integrated. Because of fixational eye motion, which is equivalent to lens motion in an optical system, every single frame from a sequence of AOSLO images (or a video) is actually an image of a different location of the retina. Such image motion, as predominantly caused by eye motion, should be compensated for before multiple images are averaged or integrated together. A conventional approach is to post-process, or offline register, these images before averaging or integrating multiple images.

Optical tracking: Diseased eyes are usually the most valuable for clinical study. Unfortunately, in many diseased eyes the eye motion is relatively large due to poor fixation. With poor fixation, offline digital registration can completely fail for AOSLO images because the overlap between the reference image and the images to be registered is either too small, or there is no overlap at all.

It is contemplated that optical eye tracking by the new system and method as described in detail hereinbelow will alleviate patient discomfort and challenges in fixating on a relatively large number of fixation target positions, such as where there is poor fixation in a target. In some embodiments, the new system and method for multi-scale closed-loop eye tracking with real-time image montaging includes a 2-D fast tip/tilt mirror (TTM) implemented in the optical path and where the position of the TTM is dynamically adjusted to track motion of the eye. Image motion from AOSLO images will be decreased significantly, although not frozen (i.e. short of a perfect or ideal correction) due to mechanical and electronic latency. After optical eye tracking these AOSLO images can be later registered in real time or post processing.

Optical steering of AOSLO imaging FOV: Traditionally, when the AOSLO needs to image the retina at one location, the subject will be asked to follow a fixation target at that location. When the AOSLO is ready to image the next retinal location, the fixation target is moved to another retinal location. In many diseased eyes, because of eye disease, the subjects are typically less able to fix on the target at some regions of the retina, and at other regions, not able to fix on the target at all. To further help solve this problem, also as described in more detail hereinbelow, in some embodiments, a second TTM has been implemented in the optical path which is able to steer AOSLO imaging FOV to any retinal location within optical capability of the system, without asking the subjects to fixate at different targets.

By optical steering, the subject fixates at only one location until the AOSLO imaging FOV runs out steering range of the optical system. Once AOSLO imaging FOV runs beyond the steering range, the subject is then asked to fixate at a different target. For example, with improved optical steering, the subject can fixate on as few as about 9 different fixation targets and the AOSLO imaging FOV can cover a retinal range ~32°×32° with the assistance of ±6° optical steering.

Montage of averaged/integrated AOSLO images: In clinical study and scientific applications, typically high SNR AOSLO images from different retinal locations are montaged (or stitched) multiple averaged (or integrated) together, with certain amount of image overlap between two adjacent locations. The montaging can be implemented in real time or with post processing.

Optical ophthalmoscope systems are generally relatively large after integration of an AOSLO and WFSLO. Also, multiple computers (e.g. PCs) have been used which make integration and operation of the software complicated. We described one such ophthalmoscope system in co-pending U.S. Provisional Patent Application Ser. No. 61/913,177, AOSLO AND WF-SLO FOR STEERABLE, STABILIZED, HIGH RESOLUTION RETINAL IMAGING AND REAL-TIME OPTICAL STABILIZATION AND DIGITAL REGISTRATION, filed Dec. 6, 2013. In U.S. Provisional Patent Application Ser. No. 61/879,961, REAL-TIME OPTICAL AND DIGITAL IMAGE STABILIZATION FOR ADAPTIVE OPTICS SCANNING OPHTHALMOSCOPY, filed Sep. 19, 2013, we described a computer software implementation. We also described an open loop WFSLO eye tracking system for an optical ophthalmoscope system in co-pending U.S. Provisional Patent Application Ser. No. 61/934,201, SYSTEMS AND METHODS FOR SIMULTANEOUS MEASUREMENT OF TEAR FILM LIPID AND AQUEOUS LAYERS THICKNESSES USING OPTICAL COHERENCE TOMOGRAPHY AND STATISTICAL ESTIMATORS, filed Jan. 31, 2014, where the scanning FOV in the slow scan direction was decreased to achieve tracking stability, with a tradeoff of increased light irradiance on the retina. We also described how while WFSLO open-loop tracking can detect a micro saccade, WFSLO open-loop tracking is typically not able to correct optically for the micro saccade. Similarly, WFSLO open-loop tracking is able to detect eye torsion, but also not able to correct for the eye torsion optically. In U.S. Provisional Application Ser. No. 62/021,510, SYSTEM AND METHOD FOR REAL-TIME MONTAGING FROM LIVE MOVING RETINA, filed Jul. 7, 2014, we described how a small field of view (FOV) of the AOSLO increases imaging time for the same retinal area, and decreases efficiency of image montaging. Also, because AOSLO and WFSLO live videos were typically displayed on two different computers, it was not easy to stack AOSLO live video on WFSLO live videos for real-time display. The '177, '961, '201, and '510 applications are incorporated herein by reference in their entirety for all purposes.

Eye of a subject: Typically, the eye of the subject is an eye of a human patient. However, in some embodiments, there can be imaging of eyes of other species of animals.

FIG. 1 shows an optical layout of one embodiment of the new optical system which employs closed-loop control from both an AOSLO and a wide-FOV camera. In the new optical system of FIG. 1, a tracking mirror is located in front of the CCD camera which is used for wide-FOV retinal imaging or pupil imaging by adjusting position of the zoom lens in front of it, and in front of the high spatial resolution AOSLO imaging system which is enclosed in the dashed rectangle. Therefore, the action of the tracking mirror to compensate for eye motion will affect image motion seen by both imaging systems.

In some embodiments of the wide-FOV imaging system, a color fast frame-rate fundus camera can be employed to image the retina. The fundus camera can be used to navigate the AOSLO imaging field to any particular retinal location with assistance from the steering mirror within its steering range.

Figure 2:
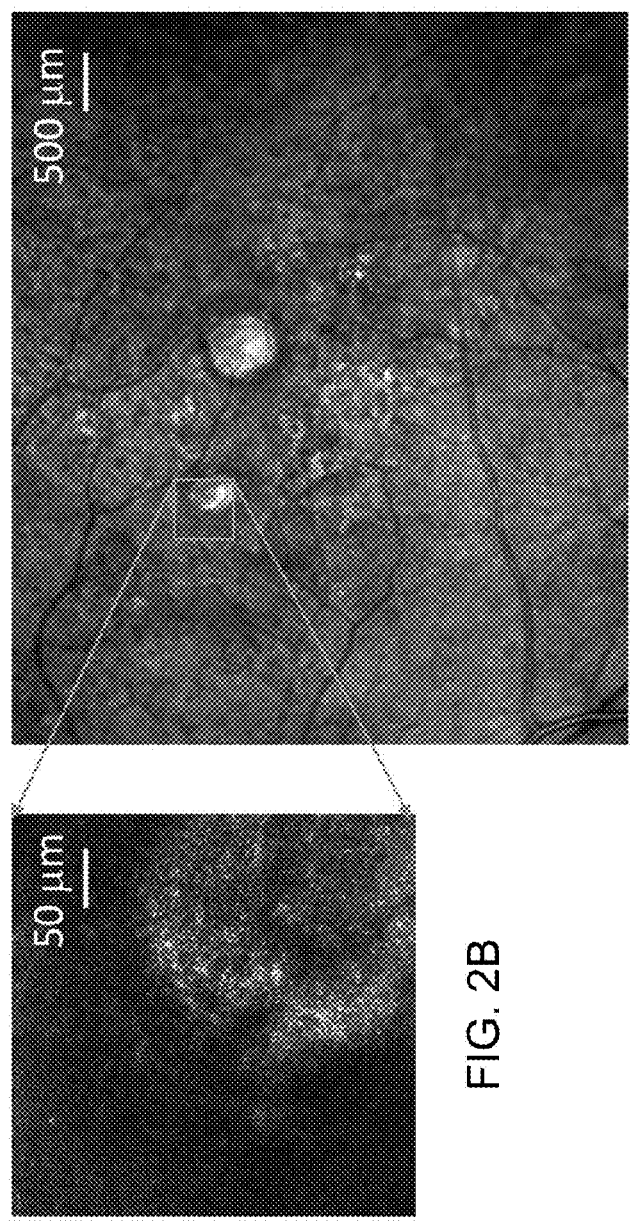
FIG. 2A shows an exemplary wide-FOV image where the block shows an area currently being imaged by a small-FOV imager.
FIG. 2B shows the exemplary small-FOV image of the block of FIG. 2A.

FIG. 2A and FIG. 2B show exemplary images which illustrate an AOSLO imaging field being navigated to a particular retinal location with the assistance of a wide-FOV camera and a steering mirror. FIG. 2A shows an exemplary wide-FOV image with the block showing an area currently being imaged by a small-FOV imager. FIG. 2B shows the exemplary small-FOV image of the block of FIG. 2A.

By use of such a fundus camera with an AOLSO, the operator can see both live AOSLO (high spatial resolution but small FOV) and wide-FOV (low spatial resolution but large FOV) videos on the same computer display (e.g. on a personal computer (PC) screen) concurrently. By such concurrent views, the operator can have a better awareness and understanding of where the retina is currently being imaged by the small-FOV AOSLO.

Also, live images from the wide-FOV camera can be used for eye tracking to compensate for eye motion in a closed loop, such as by dynamically steering one or more tracking mirrors. In some embodiments a rotational stage can be used in combination to stabilize live images on both AOSLO and the wide-FOV camera.

Example of a suitable wide FOV fundus camera: The Sony DFK 23U618 (available from the Sony Corp of Japan) is a good candidate for the wide-FOV camera. Via a standard USB 3.0 interface, the exemplary Sony camera can output 640×480 pixels/frame RGB32 color images at 120 frames/second. The fundus image can be in color instead of black and white, which shows less information. The exemplary Sony camera has pixel size 5.6 µm/pixel. For example, with an optical amplification of 3, it will be possible to obtain images from the retina of about (640×5.6×3) µm×(480×5.6× 3)≈10.8 mm×8.1 mm which is equivalent to ~36°×27° FOV. The optical amplification can be adjusted in a physical optical system hence FOV of the imaging system is also adjustable.

Translational and torsional eye movements: During clinical imaging, eye motion appearing on both AOSLO images and wide-FOV fundus images generally includes not only translation, but also torsion. Typically, the eye torsion is represented as image rotation.

Embodiments that include an eye tracking implementation measure the amount of eye torsion from information of image rotation. In those embodiments, the torsion data can be applied to a rotational stage to compensate for eye torsion in a closed loop substantially in real time. Such a rotational stage (not shown in FIG. 1) can be employed in the optical system in FIG. 1 to rotate A) the whole optical axis from both AOSLO and the fundus camera, B) to rotate the chin rest for the subject, and/or C) to rotate the resonant scanner and the slow scanner of AOSLO. Exemplary optical and mechanical implementations of these three approaches for torsion compensation are illustrated in FIG. 3, FIG. 4, and FIG. 5 respectively.

Figure 3:
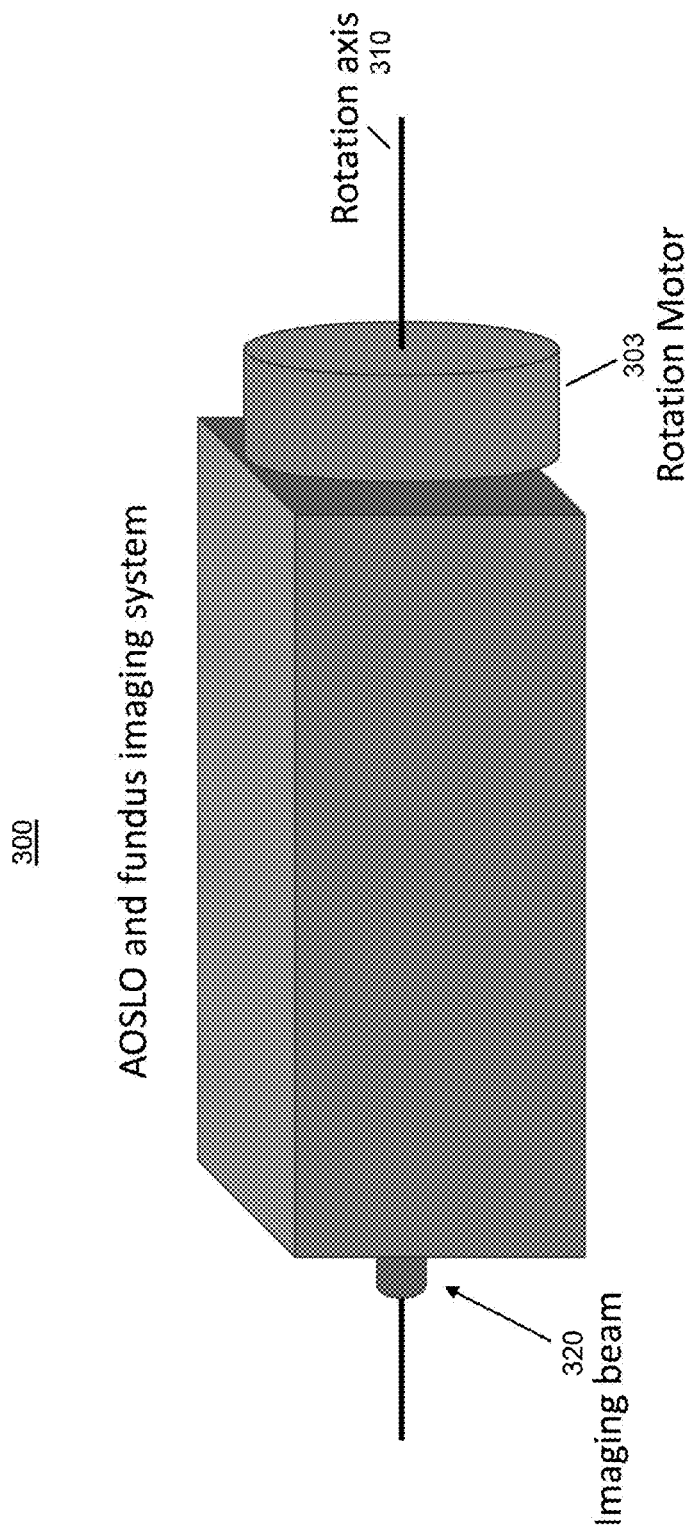
FIG. 3 shows an exemplary real-time closed-loop compensation for eye torsion the whole optical axis of both the AOSLO and the fundus camera is rotated.

FIG. 3 shows an exemplary real-time closed-loop compensation for eye torsion by rotating both AOSLO and the fundus camera about the optical axis 310 using a rotation motor 303. In FIG. 3, the rotation optical axis 310 is substantially co-axial with the imaging light beam 320.

FIG. 4A, FIG. 4B, FIG. 4C, FIG. 4D, and FIG. 4E shows drawings of an exemplary real-time closed-loop compensation for eye torsion. FIG. 4A shows an isometric drawing of the rotating chin rest system 400. The real-time closed-loop compensation for eye torsion rotates rotating mount 401 with chin rest 405 by use of a motor 403. The rotational axis 410 is substantially co-axial with the imaging light. FIG. 4B is a drawing showing a front face view of a human subject resting his chin in chin rest 405. FIG. 4C shows a side view of the rotating mount 401 and motor 403 of FIG. 4B. FIG. 4D shows a rear view of the back of the rotating mount 401 and motor 403 of FIG. 4B. FIG. 4E shows an angled side view of the rotating mount 401 and motor 403 of FIG. 4B.

Torsional correction device: Any suitable actuator which causes a rotational movement can be used as a torsional correction device, such as for embodiments which rotate either or both of the AOSLO apparatus and the wide FOV camera, or which rotate the head and/or chin mount fixture. Typically, the torsional correction device can be any type of suitable motor. Suitable types of motors include, for example, the Aerotech AGC-245 available from Aerotech, Inc. of Pittsburgh, Pa. It is understood that there can also be rotational or angular feedback devices to report to the computer the actual rotation angle of a rotational stage or rotational head and/or chin mount fixture. Such angular sensors can be provided internal to the torsional correction device (e.g. a motor) or external to the torsional correction device (e.g. mechanically coupled to a motor shaft).

Figure 5A:
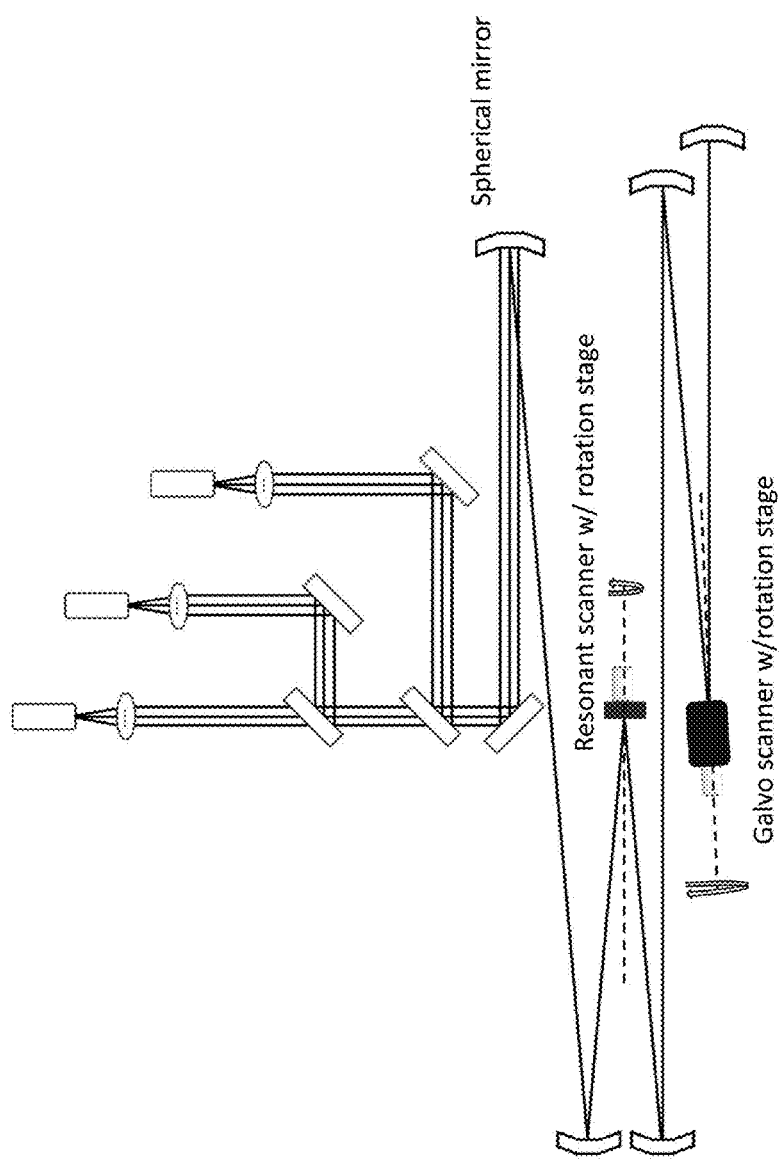
FIG. 5A shows an optical schematic diagram of an exemplary real-time closed-loop compensation system for eye torsion.
Figure 5E:
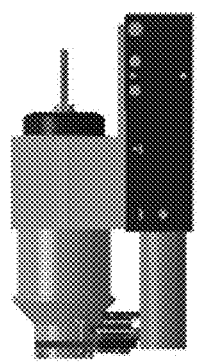
FIG. 5E shows a side view of the rotating resonant scanner and slow scanner of FIG. 5C.
Figure 5F:
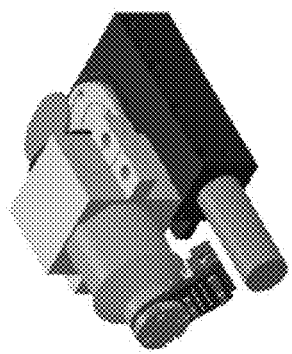
FIG. 5F shows another isometric view of the rotating resonant scanner and slow scanner of FIG. 5C.
Figure 5C:
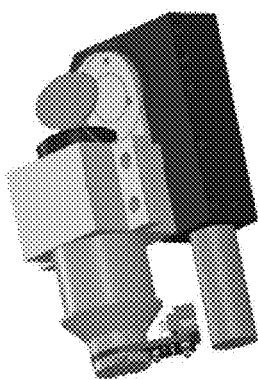
FIG. 5C shows an isometric view of an exemplary rotating resonant scanner and slow scanner.
Figure 5D:
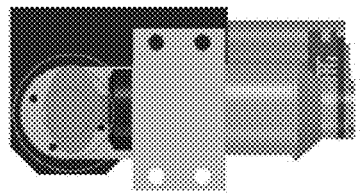
FIG. 5D shows a top view of the rotating resonant scanner and slow scanner of FIG. 5C.
Figure 5B:
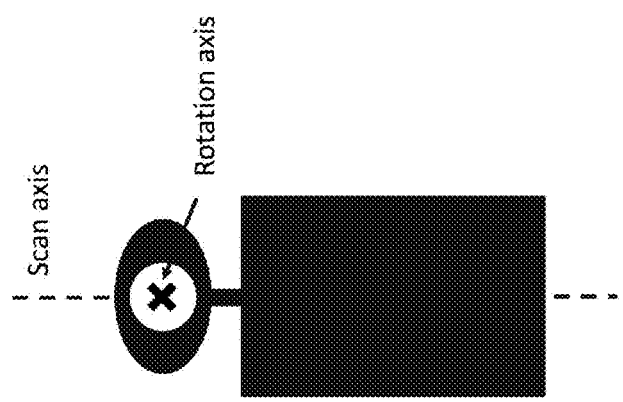
FIG. 5B shows a block diagram representation of the rotating resonant scanner and slow scanner of FIG. 5A.

FIG. 5A shows an optical schematic diagram of an exemplary real-time closed-loop compensation for eye torsion implemented by rotating scanning direction of the resonant scanner and the slow scanner. FIG. 5B shows a block diagram representation of the rotating resonant scanner and slow scanner of FIG. 5A. FIG. 5C shows an isometric view of an exemplary rotating resonant scanner and slow scanner. In the exemplary embodiment of FIG. 5A, FIG. 5B and FIG. 5C, the rotation plane is parallel with the mirror surface and the rotation axis is orthogonal with the mirror surface at the surface center point. FIG. 5D shows a top view of the rotating resonant scanner and slow scanner of FIG. 5C. FIG. 5E shows a side view of the rotating resonant scanner and slow scanner of FIG. 5C. FIG. 5F shows another isometric view of the rotating resonant scanner and slow scanner of FIG. 5C.

In this application, closed-loop eye tracking typically compensates for two different eye motions in both AOSLO and the wide-FOV camera: A) translation and B) torsion. For simplicity, in some of the exemplary embodiments which follow these two parts are decoupled in the description hereinbelow, however the tracking system effectively combines them together.

To substantially increase the robustness of eye tracking, exemplary embodiments (e.g. FIG. 1) allow both the fundus camera system and the AOSLO to "see" the action of the tracking mirror. An image-based strip-level algorithm, such as has been described in U.S. Provisional Patent Application Ser. No. 61/929,568, SYSTEM AND METHOD FOR REAL-TIME IMAGE REGISTRATION, filed Jan. 21, 2014, is implemented to detect image motion from both the live AOSLO images and the live wide-FOV camera individually. When the tracking mirror starts working, both the AOSLO and the wide-FOV camera "see" residual image motion only, hence both cameras are working within their own closed loop. The '568 application is incorporated herein by reference in its entirety for all purposes.

Figure 6:
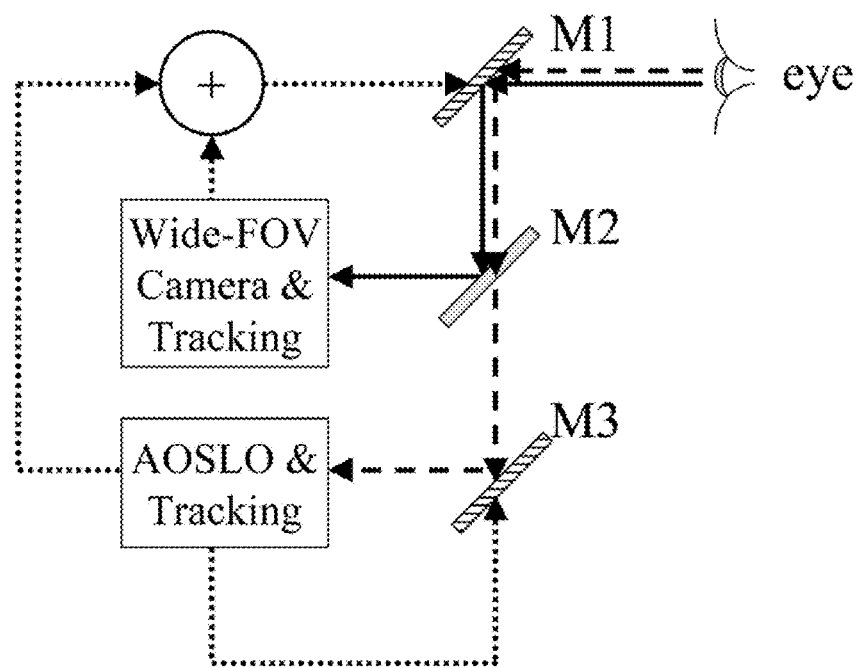
FIG. 6 shows a diagram illustrating an exemplary complete based closed-loop tracking system.

FIG. 6 shows a diagram which illustrates such an exemplary computer based closed-loop tracking system with additional steering capability from AOSLO. The solid and dashed arrows show optical paths, and the dotted arrows are electronic paths. M1 is the tracking mirror compensating for eye motion for both AOSLO and the wide-FOV camera, M2 is a beam splitter, and M3 is a steering mirror which can also join AOSLO eye tracking.

In the exemplary embodiment of FIG. 6 as contemplated, M1 is a two-dimensional fast tracking mirror or two fast one-dimensional tracking mirrors which are the same as the tracking mirror in FIG. 1. For fast mechanical response, large optical tracking range and sufficient resolution with low cost, a galvano scanning mirror (VM2500+ for one-dimensional or 6240 H for two-dimensional mirror, Cambridge Technology, Bedford, Mass.) will be employed for M1. M1 receives tracking signal (translation) from both AOSLO and the wide-FOV camera in the form of, $$(x_{t+1}, y_{t+1}) = (x_t, y_t) + g_{ao}(\Delta x_{t,ao}, \Delta y_{t,ao}) + g_{wf}(\Delta x_{t,wf}, \Delta y_{t,wf}) \quad (1)$$

where $(\Delta x_{t,ao}, \Delta y_{t,ao})$ is residual image motion detected by AOSLO at time t, $(\Delta x_{t,wf}, \Delta y_{t,wf})$ is residual image motion detected by the wide-FOV camera at time t, $g_{ao}$ and $g_{wf}$ are closed-loop gains from AOSLO and wide-FOV camera respectively, $(x_t, y_t)$ is accumulated motion of M1 at time t, and $(x_{t+1}, y_{t+1})$ is new motion of M1 to be updated. M2 is a dichroic beam splitter where the optical path with solid arrows goes to wide-FOV camera, and the optical path with dashed arrows goes to AOSLO. M3 is a 2D steering mirror, or two 1D steering mirrors, or a steering mirror such as a galvano scanning mirror installed on a rotational stage.

One or both dimensions of M3 will optionally join AOSLO tracking and the slow scanner in AOSLO (in the dashed rectangle in FIG. 1) and will also optionally join AOSLO tracking. When eye motion is too large and M1 saturates, the additional motion will be automatically offloaded to M3 and the slow scanner in AOSLO.

With the optical implementation of FIG. 1 and the closed-loop tracking of FIG. 6, plus a mechanically fast tracking mirror M1, it is contemplated that micro saccades will be detected and optically compensated for from the wide-FOV system and AOSLO, due to two improvements.

A) M1 will be activated immediately when a larger-than-usual (e.g. a micro saccade) eye motion is detected. Even if there is occasionally failed motion detection, the close-loop control system has the ability of self-correction to keep eye tracking system stable.

B) Algorithm of wide-FOV tracking and AOSLO tracking runs in the same computer (e.g. in some embodiments, a PC) memory space, AOSLO tracking algorithm will be notified by wide-FOV tracking algorithm immediately about the status of a micro saccade, and AOSLO will adjust its tracking algorithm dynamically to compensate for the residual motion from a micro saccade. The integration of data acquisition and tracking algorithm is described in more detail hereinbelow.

Detection and compensation for eye torsion: Besides compensating for translational eye motion shown in Equation (1), the new systems as described herein have the ability to detect and compensate for eye torsion. Eye torsion is not visible during short imaging session, e.g., less than 10 seconds, from a healthy eye with good fixation. However, eye torsion is typically associated with diseased eyes with poor fixation which usually have the most clinical values. In the new implementations described herein, one of the two 2-D rigid body image registration algorithms [1, 2] will be employed on the wide-FOV camera to detect eye torsion concurrently at frame rate of the wide-FOV camera, e.g., 120 Hz with the exemplary Sony camera described hereinabove. It is reasonable to treat the retina as a rigid body when the imaging FOV is ~36°×27° and the camera takes a snap shot in every 1/120 second. The translation is feedback to M1 in the amount of $g_{wf}(\Delta x_{t,wf}, \Delta y_{t,wf})$ in Equation (1) and the torsion (rotation) part is feedback to the rotational stage as shown in FIG. 3, FIG. 4 and FIG. 5. Therefore, both the tracking of eye translation and torsion from the wide-FOV is working in a closed loop.

Figure 7:
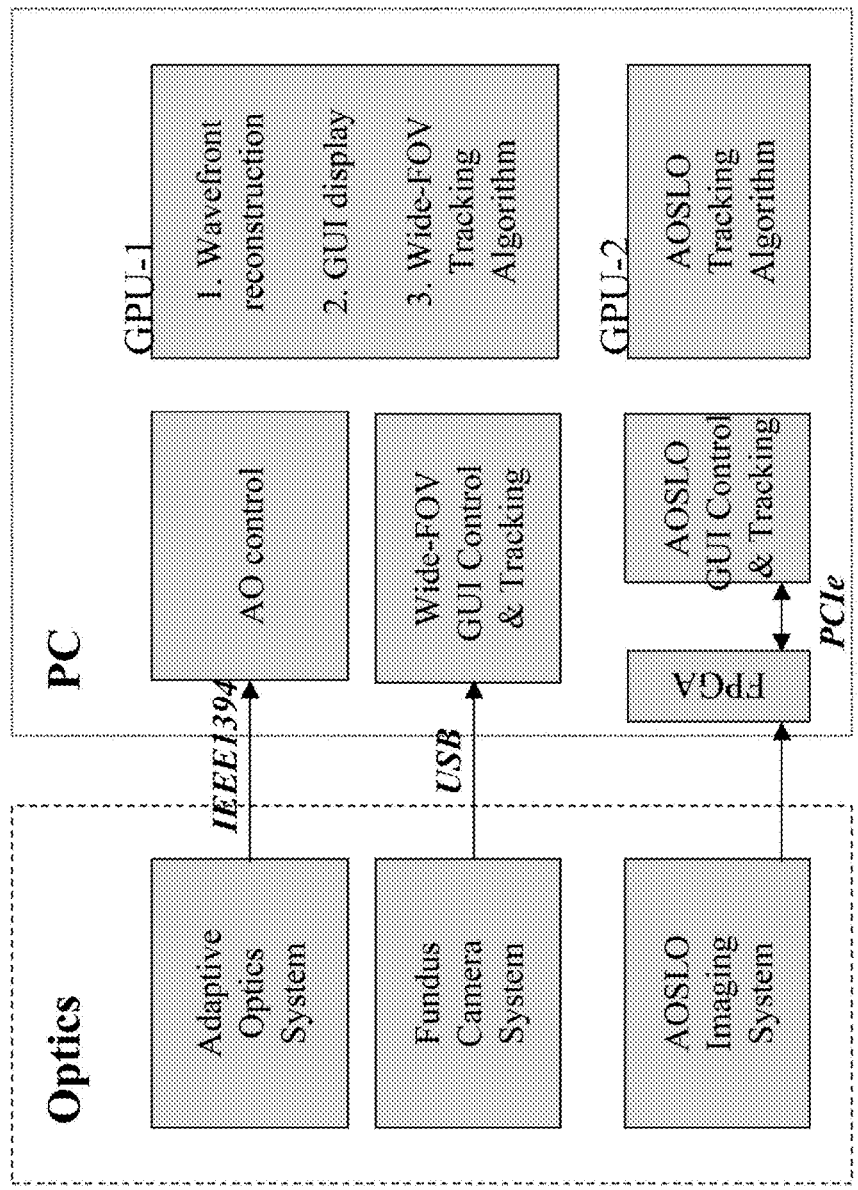
FIG. 7 shows a block diagram illustrating data flow for an exemplary single computer implementation of a multi-scale eye-tracking system.

Exemplary suitable implementations of AOSLO tracking can implement the same strip-level algorithm as were described in the '568 application, with the additional detection of eye torsion described in the '201 application. The translation provides feedback to M1 in the amount of $g_{ao}(\Delta x_{t,ao}, \Delta y_{t,ao})$ in Equation (1) and the torsion is feedback to the rotational stage described in FIG. 3, FIG. 4, or FIG. 5. Therefore, the tracking of eye translation and torsion from AOSLO is also working in a closed loop. The compensation for eye torsion is presented in the form of, $$V_{t+1} = V_t + g'_{ao}\Delta V_{t,ao} + g'_{wf}\Delta V_{t,wf} \quad (2)$$

where $\Delta V_{t,ao}$ and $\Delta V_{t,wf}$ are the detected amount of torsion from AOSLO and wide-FOV camera, $g'_{ao}$ and $g'_{wf}$ are the closed-loop gains for the compensation of eye torsion, and $V_t$ is the accumulated amount of torsion on the rotational stage, and $V_{t+1}$ is the new amount torsion to be applied on the rotational stage. With the torsion compensation from FIG. 5, the part of $g'_{wf}\Delta V_{t,wf}$ will not be applied because the wide-FOV camera does not see the action of the resonant scanner of AOSLO Exemplary Implementation of data acquisition and data processing: a suitable data flow is illustrated in FIG. 7 which can be used to merge the data acquisition and data processing into one computer (e.g. into one PC). A one-PC solution for multiple scale eye tracking with wavefront correction involves significant complexity of the optical and electronics systems. The integration of multiple channels data I/O on one PC is described in more detail in the example which follows.

In one exemplary embodiment, the system includes three sub systems: A) an adaptive optics control system to compensate for optical aberrations from the live eyes, B) a wide-FOV imaging system to acquire live retinal image from large FOV with low spatial resolution, and C) an AOSLO system to acquire live retinal image from a small FOV, but with high spatial resolution. Each sub system has its own data path. In the exemplary implementation of FIG. 7, the data path from each sub system is completely isolated, where data from adaptive optics system goes to PC through the interface of IEEE-1394, data from the fundus camera goes to PC through the interface of USB 3.0, and data from the imaging system goes to PC through the interface of PCIe. This isolation of data path avoids potential conflicts in PC interrupt handling. Multiple nVidia GPU's, e.g., GTX750, GTX760, or any new nVidia product (nVidia Corp, Santa Clara, Calif.) will be employed for data processing and live video display. For example, GPU-1 is used to A) wavefront reconstruction of adaptive optics, and B) PC monitor display. GPU-2 is used to running tracking algorithm for the wide-FOV fundus camera. GPU-3 (and more) is used for AOSLO, including but not limited to, running tracking algorithm, real-time image registration, real-time image averaging, data integration, and montaging AOSLO images from multiple overlapped retinal areas.

Example: FIG. 7 shows a block diagram illustrating data flow for an exemplary single computer implementation of a multi-scale eye-tracking system. By single computer, we refer to a single personal computer (PC) in the exemplary embodiment. It will be understood by those skilled in the art, that in other embodiments, a single computer implementation could alternatively use any suitable work station, or any other suitable single computer, such as, for example, a single computer running the Apple OS or a single computer running a LINUX OS. It is understood, for example, that where some hardware boards might be, for example, only PC or MAC compatible, the alternate hardware and/or OS user can use a computer hardware and/or OS suitable alternative board.

In the exemplary embodiment of FIG. 7, a new generation of FPGA module is employed, and it is currently a Xilinx (Xilinx Inc., San Jose, Calif.) Virtex-6 based ML605, but the new generation Kintex-7 based KC705, more advanced Virtex-7 based VC707, or any future low-cost FPGA modules will be considered. These exemplary FPGA boards have the flexibility to receive digitized data from multiple channels (four or more) of Analog-to-Digital device (A/D), and to send digital data to multiple channels of Digital-to-Analog device (D/A). Texas Instruments (TI, Austin, Tex.) ADS58C48-EVM is currently used for data acquisition from AOSLO, and Texas Instrument's DAC5672-EVM and other D/A modules to control external device such as the tracking mirror and the steering mirror. Through the FPGA, additional slow but high-resolution D/A, e.g., TI's DAC8728-

EVM, are programmed to output gains of the photomultipliers and the resonant scanner. The FGPA board can be mounted in an instrument, in the computer (e.g. in the computer cabinet of a single computer solution), or be used as an additional circuit board (typically in an enclosure outside of the instrument R&D environment) with suitable interconnections to the instruments and computer. It will be understood by those skilled in the art that in some embodiments, another processor (beyond the processor of the computer in a single computer solution) can be substituted for the exemplary FPGA, such as, for example, a suitable digital signal processor (DSP).

Figure 8:
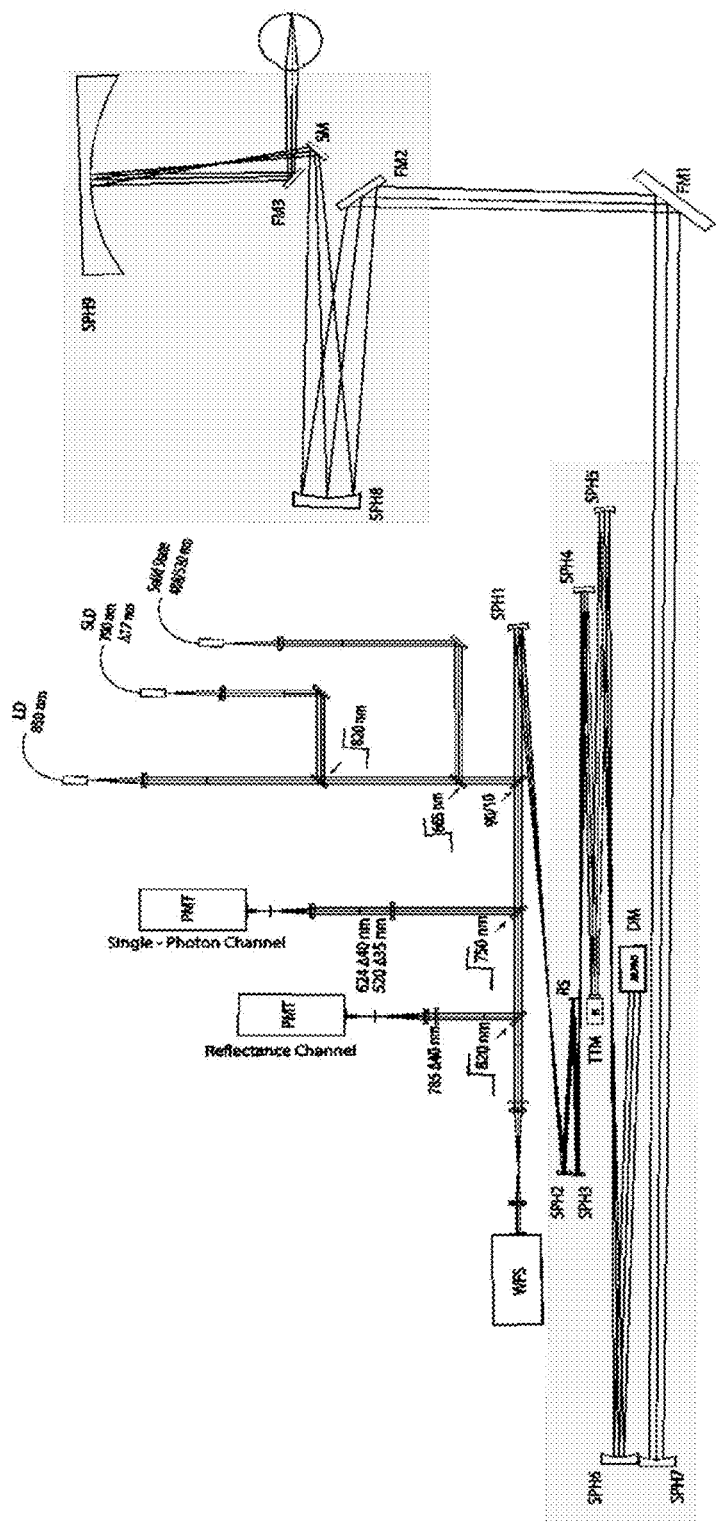
FIG. 8 shows a schematic diagram of an exemplary AOSLO system with 2.4° imaging FOV and ±12° optical steering range.

In order to increase imaging efficiency and decrease imaging time, this new system has about a 2.4° imaging FOV from AOSLO and about a ±12° optical steering range from M3 in FIG. 6. The layout of this new system is illustrated in FIG. 8.

Imaging software of AOSLO uses data from both forward scan and backward scan of the resonant scanner to achieve sufficient pixel resolution, and then performs line interlace to double the image size or image frame rate, or does frame interlace to double the frame rate.

Example: Using a typical 15.7 kHz resonant scanner (EOPC SC-30 with or without SH-65. EOPC, Electro-optical Product Corp., Fresh Meadows, N.Y.) and a slow scanner, AOSLO images at 25 frames per second can be achieved, with $$15700(\text{lines/second})/25(\text{frame/second})=628(\text{lines/frame}) \quad (3)$$

where 600 lines in Eq. (3) are used for imaging, and the rest 28 lines are used for retracing of the slow scanner. The number of pixels per line is arbitrary dependent on the parameters from the digitizer.

Large AOSLO imaging FOV (2.4°) and large image size (1200×1200 pixels) can facilitate convenient and efficient image montaging. With the assistance of closed-loop eye tracking for both translation and torsion from AOSLO and the wide-FOV camera, it is contemplated that the residual AOSLO image motion will be only ~0.1°–0.15°. An overlap of 0.4° between two adjacent retinal locations will be sufficient for montaging (or stitching) multiple images from adjacent retinal areas. Therefore, sweeping through a 24°× 24° retinal area with this new invention needs to image only ~12×12 retinal locations to achieve an image montage at ~14400×14400 pixels. With existing technology, at least ~20×20 locations are required to image the same amount of retinal area To reduce unnecessary light exposure, the light source of AOSLO will be optically turned off when the scanners run out of the imaging FOV. This means that the light source will be turned on only when data acquisition occurs. In one exemplary embodiment, this feature to turn the light source off when data acquisition is not occurring, has been implemented by sending a TTL signal to the modulation input port of the LED light source e.g., SuperLum S790 or S680 (SuperLum, Co. Cork, Ireland) to turn on/off the light source. In the exemplary embodiment, there is no additional cost besides one BNC cable routing a TTL signal from FPGA to each LED light source.

In some embodiments, to increase the signal to noise ratio (SNR) of the raw image from AOSLO we optionally oversample the analog to digital converter (A/D), and then implement pixel-binning technology on any suitable pixel-binning hardware. For example, the system for multi-scale closed-loop eye tracking described hereinabove can further include an over-sampling analog to digital converter (A/D) in combination with a pixel-binning process algorithm which runs on a pixel-binning hardware. The pixel-binning hardware can be any suitable gate array or processor, such as, for example, a field programmable gate array or digital signal processor (DSP) to increase a signal to noise ratio (SNR) of a raw image from the AOSLO imaging apparatus. The pixel-binning process algorithm while typically running on a dedicated pixel-binning hardware can in some embodiments share an FPGA (e.g. as described hereinabove) or DSP which performs other system functions. The pixel-binning hardware can be located on a card in or associated with the AOSLO instrument, in the computer enclosure of a single computer solution, or in a separate hardware enclosure.

Example: If the imaging system has a native 33 MHz pixel clock, the A/D will receive a 4×33 MHz=132 MHz pixel clock from FPGA, and output 132 M samples per second to the FPGA. The FPGA does 4→1 binning by combining 4 pixels to 1 pixel, and then sends the result to the PC. Because the binning is completed on FPGA, it does not increase any processing burden on the host PC and the communication bandwidth between host PC and FPGA. With the exemplary 11-bit ADS58C48 from TI, the advantage is that each pixel is increased from 11 bits to 13 bits which increases dynamic range of the image and increase the SNR by a factor of 2.

Firmware and/or software for systems described hereinabove can be provided on and/or reside on a computer readable non-transitory storage medium. A computer readable non-transitory storage medium as non-transitory data storage includes any data stored on any suitable media in a non-fleeting manner. Such data storage includes any suitable computer readable non-transitory storage medium, including, but not limited to hard drives, non-volatile RAM, SSD devices, CDs, DVDs, etc.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

REFERENCE

1. M. Sochor, MATLAB™ Central, <http://www.mathworks.com/matlabcentral/fileexchange/19086-automatic-2d-rigid-body-image-registration>.
2. C. A. Wilson and J. A. Theriot, A correlation-based approach to calculate rotation and translation of moving cells, IEEE Transaction on Imaging Processing, Vol. 15, No. 7, July 2006.

What is claimed is:

1. A system for multi-scale closed-loop eye tracking to compensate for translation and rotation motion while imaging in vivo a surface area of an internal structure of an eye of a subject comprising:
   a narrow field imaging device optically coupled to an optical path to receive light reflected from the surface area of the structure of the eye;
   a wide field camera optically coupled to the optical path by a beam splitter disposed in said optical path;
   a tracking mirror disposed in said optical path between said beam splitter and the structure of the eye;
   a torsional correction device mechanically coupled to one or more optical components of the system;

a control process algorithm running on a computer, said computer communicatively coupled to said wide field camera and said narrow field imaging device and said tracking mirror and said torsional correction device, and wherein said control process algorithm causes movements of said tracking mirror and said torsional correction device to actively compensate substantially in real time for both translational and rotational movements of the eye at least in part based on feedback images from said wide field camera and said narrow field imaging device; and an additional steering mirror disposed in said optical path between said narrow field imaging device and said beam splitter, said additional steering mirror communicatively coupled to said computer and controlled by said control process algorithm to provide an additional translational correction.

2. The system for multi-scale closed-loop eye tracking of claim 1, wherein said wide field camera comprises a Fundus camera.

3. The system for multi-scale closed-loop eye tracking of claim 1, wherein said narrow field imaging device comprises an AOSLO imaging apparatus.

4. The system for multi-scale closed-loop eye tracking of claim 3, wherein said AOSLO imaging apparatus is optically turned off when an AOSLO scanner runs out of an imaging FOV.

5. The system for multi-scale closed-loop eye tracking of claim 3, further comprising an over-sampling analog to digital converter (A/D) in combination with a pixel-binning process algorithm which runs on a pixel-binning hardware to increase a signal to noise ratio (SNR) of a raw image from said AOSLO imaging apparatus.

6. The system for multi-scale closed-loop eye tracking of claim 1, wherein said tracking mirror comprises at least one or more galvano scanning mirrors.

7. The system for multi-scale closed-loop eye tracking of claim 1, wherein said wide field camera and said narrow field imaging device are mounted on a rotational stage mechanically coupled to said torsional correction device.

8. The system for multi-scale closed-loop eye tracking of claim 1, wherein either of said wide field camera or said narrow field imaging device, is mounted on a rotational stage mechanically coupled to said torsional correction device.

9. The system for multi-scale closed-loop eye tracking of claim 8, wherein said torsional correction device comprises a motor.

10. The system for multi-scale closed-loop eye tracking of claim 1, wherein said system comprises an integration of multiple channels of data I/O on a single personal computer (PC).

11. A system for multi-scale closed-loop eye tracking to compensate for translation and rotation motion while imaging in vivo a surface area of an internal structure of an eye of a subject where a subject's head is supported by the system comprising:

a narrow field imaging device optically coupled to an optical path to receive light reflected from the surface area of a structure of the eye;

a wide field camera optically coupled to the optical path by a beam splitter disposed in said optical path;

a tracking mirror disposed in said optical path between said beam splitter and the structure of the eye;

a torsional correction device comprising a rotating mount which rotates the subject's head in a plane about parallel to a surface of the surface area of the structure of the eye, said rotating mount comprising a chin rest at a first end of said rotating mount, said rotating mount extending from rearward from said first end of said rotating mount to a second end of said rotating mount behind the subject's head, and a motor mechanically and rotatingly coupled said second end of said rotating mount; and a control process algorithm running on a computer, said computer communicatively coupled to said wide field camera and said narrow field imaging device and said tracking mirror and said torsional correction device rotating mount, and wherein said control process algorithm causes movements of said tracking mirror and said motor of said torsional correction device rotating mount to actively compensate substantially in real time for both translational and rotational movements of the eye, at least in part based on feedback images from said wide field camera and said narrow field imaging device.

12. A method for multi-scale closed-loop eye tracking to compensate for translation and rotation motion while imaging in vivo a surface area of an internal structure of an eye of a subject's head comprising:

providing a narrow field imaging device optically coupled to an optical path to receive light reflected from the surface area of the structure of the eye, a wide field camera optically coupled to the optical path by a beam splitter disposed in said optical path, a tracking mirror disposed in said optical path between said beam splitter and the structure of the eye, a torsional correction device, and a control process algorithm running on a computer;

calculating by computer a translation and a rotation of the eye at least in part from an image received from said wide field camera and said narrow field imaging device; and setting by computer a position of said tracking mirror to compensate for said translation of the eye and setting by computer a rotational movement of said torsional correction device, to compensate for said rotation of the eye, and setting by computer said torsional correction device which rotates both of said wide field camera and said narrow field imaging device to compensate for said rotation of the eye.

13. A system for multi-scale closed-loop eye tracking to compensate for translation and rotation motion while imaging in vivo a surface area of an internal structure of an eye of a subject comprising:

a narrow field imaging device optically coupled to an optical path to receive light reflected from the surface area of the structure of the eye;

a wide field camera optically coupled to the optical path by a beam splitter disposed in said optical path;

a tracking mirror disposed in said optical path between said beam splitter and the structure of the eye;

a torsional correction device mechanically coupled to one or more optical components of the system;

a control process algorithm running on a computer, said computer communicatively coupled to said wide field camera and said narrow field imaging device and said tracking mirror and said torsional correction device, and wherein said control process algorithm causes movements of said tracking mirror and said torsional correction device to actively compensate substantially in real time for both translational and rotational movements of the eye at least in part based on feedback images from said wide field camera and said narrow field imaging device; and an over-sampling analog to digital converter (A/D) in combination with a pixel-binning process algorithm which runs on a pixel-binning hardware to increase a signal to noise ratio (SNR) of a raw image from said AOSLO imaging apparatus.

14. The system for multi-scale closed-loop eye tracking of claim 13, wherein said wide field camera comprises a Fundus camera.

15. The system for multi-scale closed-loop eye tracking of claim 13, wherein said narrow field imaging device comprises an AOSLO imaging apparatus.

16. The system for multi-scale closed-loop eye tracking of claim 15, wherein said AOSLO imaging apparatus is optically turned off when an AOSLO scanner runs out of an imaging FOV.

17. The system for multi-scale closed-loop eye tracking of claim 13, wherein said tracking mirror comprises at least one or more galvano scanning mirrors.

18. The system for multi-scale closed-loop eye tracking of claim 13, wherein said wide field camera and said narrow field imaging device are mounted on a rotational stage mechanically coupled to said torsional correction device.

19. The system for multi-scale closed-loop eye tracking of claim 13, wherein either of said wide field camera or said narrow field imaging device, is mounted on a rotational stage mechanically coupled to said torsional correction device.

20. The system for multi-scale closed-loop eye tracking of claim 19, wherein said torsional correction device comprises a motor.

21. The system for multi-scale closed-loop eye tracking of claim 13, wherein said system comprises an integration of multiple channels of data I/O on a single personal computer (PC).

* * * * *